(12) United States Patent
Kanno et al.

(10) Patent No.: US 9,504,752 B2
(45) Date of Patent: Nov. 29, 2016

(54) STERILIZER, ORAL CAVITY STERILIZER, STERILIZATION METHOD, STERILIZATION APPARATUS, AND STERILIZER EVALUATION METHOD

(75) Inventors: Taro Kanno, Sendai (JP); Keisuke Nakamura, Sendai (JP); Hiroyo Ikai, Sendai (JP); Masahiro Kono, Sendai (JP); Yoshimi Niwano, Sendai (JP)

(73) Assignee: AZ CO., LTD., Sendai-Shi (JP)

( * ) Notice: Subject to any disclaimer, the term of this patent is extended or adjusted under 35 U.S.C. 154(b) by 0 days.

(21) Appl. No.: 14/361,605

(22) PCT Filed: Dec. 1, 2011

(86) PCT No.: PCT/JP2011/077864
§ 371 (c)(1),
(2), (4) Date: May 29, 2014

(87) PCT Pub. No.: WO2013/080366
PCT Pub. Date: Jun. 6, 2013

(65) Prior Publication Data
US 2014/0334976 A1 Nov. 13, 2014

(51) Int. Cl.
| | |
|---|---|
| A61K 33/40 | (2006.01) |
| A61K 47/46 | (2006.01) |
| A61K 36/82 | (2006.01) |
| A61K 36/539 | (2006.01) |
| A61L 2/00 | (2006.01) |
| C12Q 1/30 | (2006.01) |

(52) U.S. Cl.
CPC ............. *A61K 47/46* (2013.01); *A61K 33/40* (2013.01); *A61K 36/539* (2013.01); *A61K 36/82* (2013.01); *A61L 2/0082* (2013.01); *C12Q 1/30* (2013.01)

(58) Field of Classification Search
CPC .... A61K 47/46; A61K 38/40; A61L 2/0082; C12Q 1/30
USPC ............................................. 422/29; 424/616
See application file for complete search history.

(56) References Cited

U.S. PATENT DOCUMENTS

| 2006/0008539 A1 | 1/2006 | Tomioka |
| 2006/0134286 A1 | 6/2006 | Maeda |
| 2010/0209411 A1 | 8/2010 | Pellico |

FOREIGN PATENT DOCUMENTS

| FR | 2 651 132 A1 | 3/1991 |
| JP | A-4-169197 | 6/1992 |
| JP | A-11-43696 | 2/1999 |
| JP | A-2006-22075 | 1/2006 |
| JP | A-2007-291028 | 11/2007 |
| JP | A-2008-284312 | 11/2008 |
| JP | A-2010-511623 | 4/2010 |
| WO | WO 03/094878 A1 | 11/2003 |
| WO | WO 2008/070387 A1 | 6/2008 |
| WO | 2008/143123 A1 | 11/2008 |

OTHER PUBLICATIONS

Phan, T.-N., et al., "Selective sensitization of bacteria to peroxide damage associated with fluoride inhibition of catalase and pseudocatalse," *Oral Microbiol Immunol*, 2001, pp. 28-33, vol. 16.
Motomura, Y. et al., "Antibacterial Effect of Crude Drugs on Bacteria Associated with Periodontitis," *Journal of the Japanese Society of Periodontology*, 1997, pp. 72-76, vol. 39, No. 1 (with Abstract).
International Search Report issued in International Application No. PCT/JP2011/077864 on Jan. 31, 2012 (with translation).
International Preliminary Report on Patentability issued in International Application No. PCT/JP2011/077864 on Aug. 10, 2012 (with translation).
Ikai, H. et al., "Photolysis of Hydrogen Peroxide, an Effective Disinfection System via Hydroxyl Radical Formation," *Antimicrobial Agents and Chemotherapy*, Dec. 2010, pp. 5086-5091, vol. 54, No. 12.
Arakawa, H. et al., "Role of Hydrogen Peroxide in Bactericidal Action of Catechin," *Biol. Pharm. Bull.*, Mar. 2004, pp. 277-281, vol. 27, No. 3.
Khan, S. et al., "Protective effect of green tea extract on gentamicin-induced nephrotoxicity and oxidative damage in rat kidney," *Pharmacological Research*, 2009, pp. 254-262, vol. 59.
Nakamura, K. et al., "A novel analytical method to evaluate directly catalase activity of microorganisms and mammalian cells by ESR oximetry," *Free Radical Research*, Sep. 2010, pp. 1036-1043, vol. 44, No. 9.
May 21, 2015 Search Report issued in European Patent Application No. 11876829.0.
Aug. 14, 2015 Written Opinion issued in Singapore Application No. 11201402799V.

*Primary Examiner* — Sean E Conley
(74) *Attorney, Agent, or Firm* — Oliff PLC

(57) ABSTRACT

It is intended to provide a sterilizer, an oral cavity sterilizer, a sterilization method, a sterilization apparatus, and a sterilizer evaluation method capable of enhancing a sterilization effect. The sterilizer including hydrogen peroxide and a catalase activity inhibitor containing *scutellaria* or green tea is brought into contact with a sterilization target. Next, the sterilization target is irradiated with light having a wavelength of 350 nm to 500 nm using a light emitting device formed of a semiconductor laser. By the light irradiation, the hydrogen peroxide is photolyzed to generate hydroxy radicals, and sterilization is achieved by the thus-generated hydroxy radicals.

6 Claims, 4 Drawing Sheets

STERILIZER, ORAL CAVITY STERILIZER, STERILIZATION METHOD, STERILIZATION APPARATUS, AND STERILIZER EVALUATION METHOD

TECHNICAL FIELD

The present invention relates to a sterilizer, an oral cavity sterilizer, a sterilization method, a sterilization apparatus, and a sterilizer evaluation method.

BACKGROUND ART

As one of conventional sterilization methods, a method of bringing a sterilization target into contact with an oxidizer such as hydrogen peroxide and then irradiating the sterilization target with light of 400 nm to 1000 nm has been known (for example, see Patent Literature 1). According to the method, hydroxy radicals are generated by irradiating the hydrogen peroxide with the light of 400 nm to 1000 nm, and the sterilization is attained by the thus-generated hydroxy radials.

CITATION LIST

Patent Literature

Patent Literature 1: JP 2008-284312 A

SUMMARY OF INVENTION

Technical Problem

The method described in Patent Literature 1 has a problem that a sterilization effect on cells and microorganisms existing on the sterilization target diminishes since a part of the hydrogen peroxide is decomposed by catalase possessed by the cells and microorganisms.

The present invention was accomplished in view of the above-described problem, and an object thereof is to provide a sterilizer, an oral cavity sterilizer, a sterilization method, a sterilization apparatus, and a sterilizer evaluation method capable of enhancing a sterilization effect.

Solution to Problem

The inventors found that catalase of cells and microorganisms existing on a sterilization target decomposes hydrogen peroxide which is a matrix for generation of hydroxy radicals having a high antibacterial property. The inventors used *Streptococcus aureus* ATCC 12693 which is a catalase-positive bacterium and *Candida albicans* JCM 9061 which is a fungus and measured DMPO-OH changes in reactions between the microorganisms and hydroxy radicals to analyze the reactions employing Lineweaver-Burk Plot. The results are shown in FIG. 1.

As shown in FIG. 1, all of the straight lines which are different in number of cells intersect at a point on the 1/DMPO concentration negative side to show not only that *S. aureus* and *C. albicans* react with the hydroxy radicals but also that catalase possessed by the microorganisms reacts with hydrogen peroxide. It should be noted that all of the straight lines different in number of cells intersect on the 1/DMPO-OH concentration axis if *S. aureus* and *C. albicans* reacted only with the hydroxy radicals and that all of the straight lines different in number of cells are parallel to each other if catalase reacted only with hydrogen peroxide.

The experiment shown in FIG. 1 was conducted by: adding 50 µL (microliter) of DMPO (5,5-dimethyl-pyrroline N-oxide) which is a 25-300 mM radical scavenger to 200 µL of each of samples which are varied in number of cells of *S. aureus* and *C. albicans*; further adding 450 µL of 0.5 M hydrogen peroxide; irradiating the mixture with LED light having a wavelength of 400±20 nm for one minute; and performing the ESR (electron spin resonance) measurement one minute after the irradiation.

From the results shown in FIG. 1, the inventors acquired knowledge that it is possible to perform efficient hydroxy radical sterilization by reducing catalase activity of cells and microorganisms by adding a catalase activity inhibitor, which led to this invention.

More specifically, a sterilizer of the present invention is characterized by comprising hydrogen peroxide and a catalase activity inhibitor to be used for performing sterilization by bringing the hydrogen peroxide and the catalase activity inhibitor into contact with a sterilization target and then irradiating the sterilization target with light having a wavelength of 350 nm to 500 nm, wherein the catalase activity inhibitor comprises *scutellaria* or green tea.

An oral cavity sterilizer according to the present invention is characterized by comprising hydrogen peroxide and a catalase activity inhibitor to be used for performing sterilization by bringing the hydrogen peroxide and the catalase activity inhibitor into contact with a sterilization target and then irradiating the sterilization target with light having a wavelength of 350 nm to 500 nm, wherein the catalase activity inhibitor comprises *scutellaria* or green tea.

The sterilizer and the oral cavity sterilizer according to the present invention are used as follows. The sterilizer or the oral cavity sterilizer according to the present invention is brought into contact with a sterilization target by applying or spraying the sterilizer or the oral cavity sterilizer onto the sterilization target. Here, owing to the catalase activity inhibitor contained in the sterilizer or the oral cavity sterilizer, catalase activity of cells and microorganisms such as catalase-positive bacterium and fungus can be reduced even when the cells and microorganisms exist on the sterilization target, and therefore a reaction between catalase and hydrogen peroxide is prevented.

Next, the sterilization target is irradiated with light of a predetermined wavelength. Since hydrogen peroxide is photolyzed by the irradiation to generate hydroxy radicals, sterilization is realized by the thus-generated hydroxy radicals. Since the catalase activity inhibitor reduces the catalase activity of the cells and microorganisms existing on the sterilization target in the above-described sterilization, too, a reduction in hydroxy radicals to be generated by the reaction between catalase and hydrogen peroxide is prevented.

As described above, the sterilizer and the oral cavity sterilizer according to the present invention are capable of preventing hydrogen peroxide which generates hydroxy radicals from being reduced due to the reaction with catalase possessed by the cells and microorganisms existing on the sterilization target and, as a result, are capable of preventing the reduction in hydroxy radicals generated from hydrogen peroxide, thereby realizing enhancement of an effect of sterilization by the hydroxy radicals.

A sterilization method according to the present invention is characterized by bringing hydrogen peroxide and a catalase activity inhibitor into contact with a sterilization target and irradiating the irradiation target with light having a wavelength of 350 nm to 500 nm.

Even if cells and microorganisms of catalase-positive bacterium and fungus existed on the sterilization target when the hydrogen peroxide and the catalase activity inhibitor are brought into contact with the sterilization target, the sterilization method according to the present invention enables to reduce catalase activity of the cells and microorganisms due to the catalase activity inhibitor and, therefore, to prevent a reaction between the catalase and the hydrogen peroxide.

Further, by the irradiation of the sterilization target with the light having wavelength of 350 nm to 500 nm, the hydrogen peroxide is photolyzed to generate hydroxy radicals, and, therefore, sterilization with the thus-generated hydroxy radicals is realized. Since the catalase activity inhibitor reduces the catalase activity of the cells and microorganisms existing on the sterilization target in the above-described sterilization, too, a reduction in hydroxy radicals to be generated by the reaction between catalase and hydrogen peroxide is prevented.

According to the sterilization method described above, the catalase activity inhibitor prevents the hydrogen peroxide which generates the hydroxy radicals from being reduced by the reaction with the catalase possessed by the cells and microorganisms existing on the sterilization target, and, as a result, the reduction in hydroxy radicals to be generated by hydrogen peroxide is prevented, thereby realizing enhancement of the effect of sterilization by hydroxy radicals.

A method for bringing the hydrogen peroxide and the catalase activity inhibitor into contact with the sterilization target in the sterilization method of the present invention may be any method and may be a method of applying or spraying the sterilizer or the oral cavity sterilizer according to the present invention, a method of immersing a sterilization target into a solution of the sterilizer according to the present invention, or the like.

A sterilization apparatus according to the present invention is characterized by comprising hydrogen peroxide, a catalase activity inhibitor, and a light emitting device which is configured to irradiate a sterilization target after being brought into contact with the hydrogen peroxide and the catalase activity inhibitor with light having a wavelength of 350 nm to 500 nm.

The sterilization apparatus according to the present invention is capable of suitably performing the sterilization method according to the present invention. With the use of the sterilization apparatus according to the present invention, the catalase activity inhibitor prevents the hydrogen peroxide which generates hydroxy radicals from being reduced by a reaction with catalase possessed by cells and microorganisms existing on the sterilization target, and, as a result, the reduction in hydroxy radicals to be generated by the hydrogen peroxide is prevented, thereby realizing enhancement of the effect of sterilization by hydroxy radicals.

In the sterilization apparatus according to the present invention, the hydrogen peroxide and the catalase activity inhibitor may be formed of the sterilizer or the oral cavity sterilizer according to the present invention. Also, in the sterilization apparatus, the sterilization target may be formed of a tooth, a denture, or the like in the oral cavity, and the catalase activity inhibitor may be formed of a tooth paste, a mouthwash, or the like comprising the catalase activity inhibitor. In this case, the hydrogen peroxide is brought into contact with the sterilization target after brushing the teeth with the tooth paste or rinsing with the mouthwash, and then the sterilization target is irradiated with the light from the light emitting device.

In the sterilization method and the sterilization apparatus according to the present invention, the light emitting device to be used for the light irradiation may be any light emitting device insofar as the light emitting device is capable of emitting the light having wavelength of 350 nm to 500 nm, and examples thereof include an incandescent lamp, a fluorescent lamp, a halogen lamp, a xenon lamp, an LED (light emitting diode), a semiconductor laser, and the like. The light to be emitted may be single wavelength light, may include a plurality of wavelengths, or may be formed of wavelengths of a predetermined band, insofar as the light has the wavelength of 350 nm to 500 nm.

In the sterilizer, the oral cavity sterilizer, the sterilization method, and the sterilization apparatus according to the present invention, the catalase activity inhibitor may preferably comprise *scutellaria*, green tea, fennel, loquat, licorice, *aloe, salvia, hamamelis*, German chamomile, rosemary, *Melissa officinalis*, or peach. Particularly, *scutellaria*, or green tea which has a high catalase activity inhibition effect may preferably be comprised.

A sterilizer evaluation method according to the present invention is characterized by performing an electron spin resonance (ESR) measurement of a mixture liquid of a sample collected from a sterilization target brought into contact with the sterilizer according to the present invention and 4-hydroxy-2,2,6,6-tetramethylpiperidine N-oxide (TEMPOL) and then evaluating a sterilization effect of the sterilizer by performing a measurement of catalase activity of cells or microorganisms contained in the sample based on a line width of the obtained electron spin resonance (ESR) spectrum.

In view of the fact that catalase catalyzes a reaction which causes decomposition of hydrogen peroxide into water and oxygen, the sterilizer evaluation method according to the present invention includes measuring the catalase activity by measuring the oxygen generated from the reaction by employing ESR oximetry. Since a positive correlation is confirmed between the line with of ESR spectrum of TEMPOL and a catalase concentration, evaluation of the sterilization effect of the sterilizer is enabled by measuring the catalase activity of cells or microorganisms contained in the sample based on the line width of the ESR spectrum. The sterilizer may be the oral cavity sterilizer according to the present invention.

Advantageous Effects of Invention

According to the present invention, it is possible to provide the sterilizer, the oral cavity sterilizer, the sterilization method, the sterilization apparatus, and the sterilizer evaluation method capable of enhancing the sterilization effect.

DESCRIPTION OF EMBODIMENTS

Figure 1:
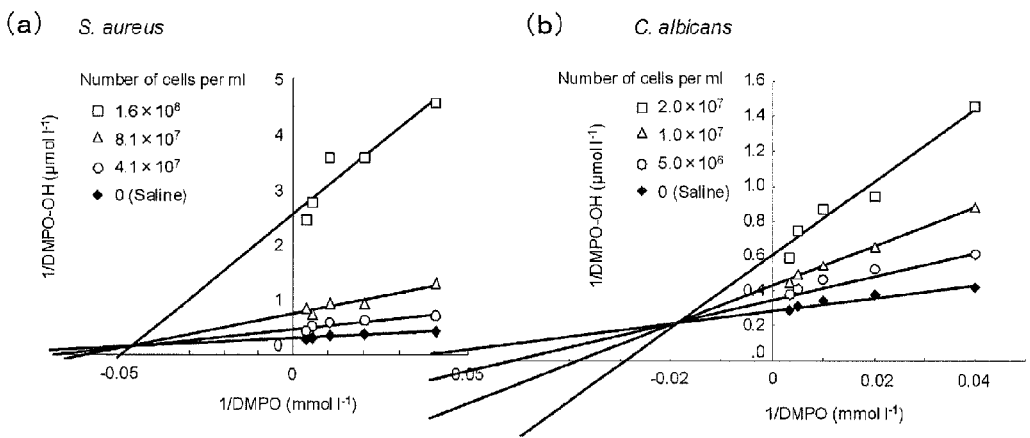
FIG. 1 is a graph showing (a) a kinetics analysis of a reaction between hydroxy radicals generated by photolysis of hydrogen peroxide and *S. aureus* and (b) a kinetics analysis of a reaction between the hydroxy radicals and *C. albicans*.

Hereinafter, a sterilizer, a sterilization method, a sterilization apparatus, and a sterilizer evaluation method according to embodiments of the present invention will be described.

The sterilization apparatus according to the embodiment of the present invention comprises the sterilizer according to the present invention and a light emitting device.

The sterilizer comprises hydrogen peroxide and a catalase activity inhibitor. The catalase activity inhibitor comprises scutellaria or green tea.

The light emitting device comprises a semiconductor which is capable of emitting light having a wavelength of 350 nm to 500 nm.

The sterilization method according to the embodiment of the present invention is suitably performed by the sterilization apparatus according to the embodiment of the present invention. Firstly, the sterilizer comprising hydrogen peroxide and a catalase activity inhibitor is brought into contact with a sterilization target. Here, even if cells and microorganisms of catalase-positive bacterium and fungus existed on the sterilization target, catalase activity thereof is reduced by the catalase activity inhibitor, and therefore the catalase is prevented from reacting with the hydrogen peroxide.

Next, the sterilization target is irradiated with light having a wavelength of 350 nm to 500 nm from the light emitting device. By the light irradiation, the hydrogen peroxide is photolyzed to generate hydroxy radicals, and sterilization is achieved by the thus-generated hydroxy radicals. Since the catalase activity inhibitor reduces the catalase activity of the cells and microorganisms existing on the sterilization target in the above-described sterilization, too, a reduction in hydroxy radicals to be generated by a reaction between the catalase and the hydrogen peroxide is prevented.

As described above, with the use of the sterilizer, the sterilization method, and the sterilization apparatus according to the embodiments of the present invention, the catalase activity inhibitor prevents the hydrogen peroxide which generates the hydroxy radicals from being reduced by the reaction with the catalase possessed by the cells and microorganisms existing on the sterilization target, and, as a result, the reduction in hydroxy radicals to be generated by the hydrogen peroxide is prevented, thereby realizing enhancement of the effect of sterilization by hydroxy radicals.

EXAMPLES

Example 1

An experiment for detecting a relationship between catalase activity and a line width of an ESR spectrum of TEMPOL was conducted. Five types of mixture liquids having final catalase concentrations of 0, 0.25, 0.5, 1.0,, and 2.0 U/mL were prepared by diluting each of 100 μL of catalase (Wako Pure Chemical Industries, Ltd.), 25 μL of TEMPOL (Sigma-Aldrich Corporation), and 125 μL of hydrogen peroxide (Santoku Chemical Industries Co., Ltd.) with ultrapure water, and mixing the thus-obtained solutions to attain the final concentrations shown in Table 1. ESR measurements of the prepared mixture liquids were conducted, and the results are shown in FIG. 2.

TABLE 1

| | Amount | Final concentration |
|---|---|---|
| Catalase | 100 μL | 0, 0.25, 0.5, 1.0, and 2.0 U/mL |
| TEMPOL | 25 μL | 200 μM |
| Hydrogen peroxide | 125 μL | 250 μM |

Figure 2:
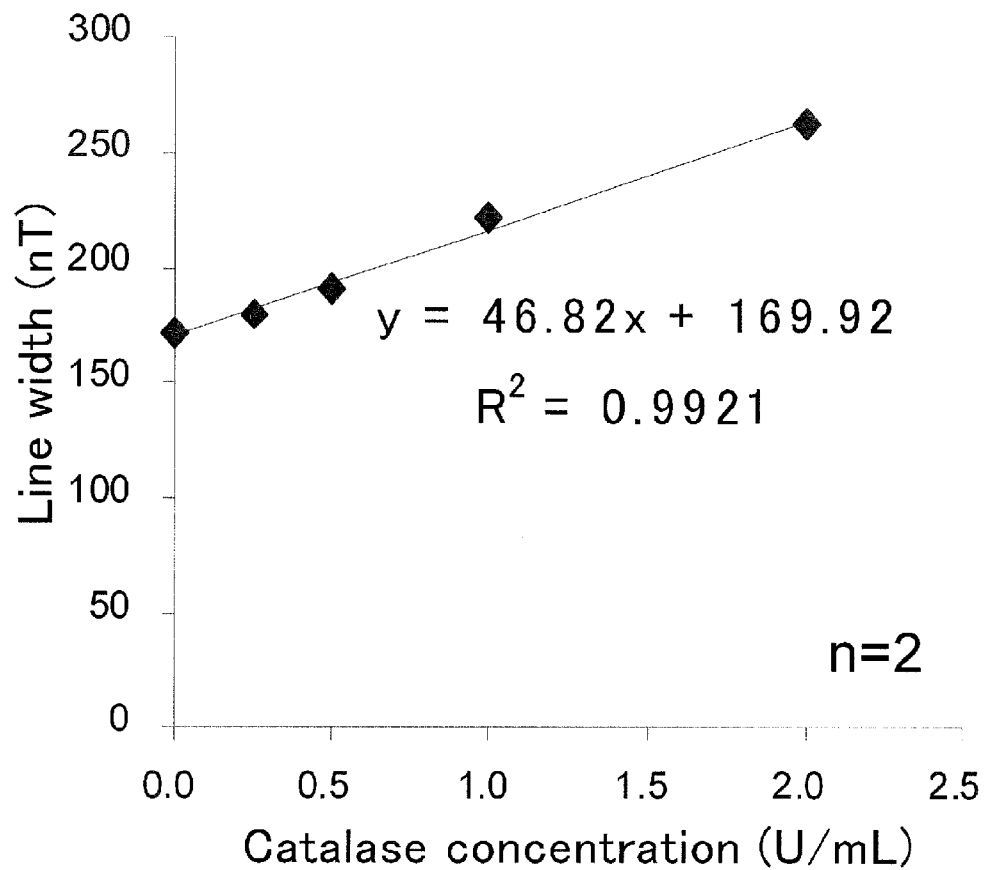
FIG. 2 is a graph showing a relationship between a catalase concentration and a line width of an ESR spectrum of TEMPOL based on a sterilizer evaluation method according to one embodiment of the present invention.

As shown in FIG. 2, it was confirmed that there is the high positive correlation between the line width of ESR spectrum of TEMPOL and the catalase concentration. From the results, it is possible to measure catalase activity of a test sample based on a line width of an ESR spectrum.

Example 2

By using the results of FIG. 2, a measurement of a catalase activity inhibitory action attained by a catalase activity inhibitor was conducted. Mixture liquids were prepared by diluting each of 50 μL of catalase, 25 μL of TEMPOL, 50 μL of a crude drug considered to have a catalase activity inhibitory action, and 125 μL of hydrogen peroxide with ultrapure water (Milli-Q water) and mixing the thus-obtained solutions to attain the final concentrations shown in Table 2. As the crude drug, scutellaria, green tea, and lemon balm were used. The crude drug was filtrated through a 0.22 μm filter in order to remove water-insoluble substances. As a comparison, a mixture liquid sample (Milli-Q water: MQ) to which no crude drug was added was prepared.

TABLE 2

| | Amount | Final concentration |
|---|---|---|
| Catalase | 50 μL | 1 U/mL |
| TEMPOL | 25 μL | 200 μM |
| Crude drug | 50 μL | 1 mg/mL |
| Hydrogen peroxide | 125 μL | 250 mM |

Figure 3:
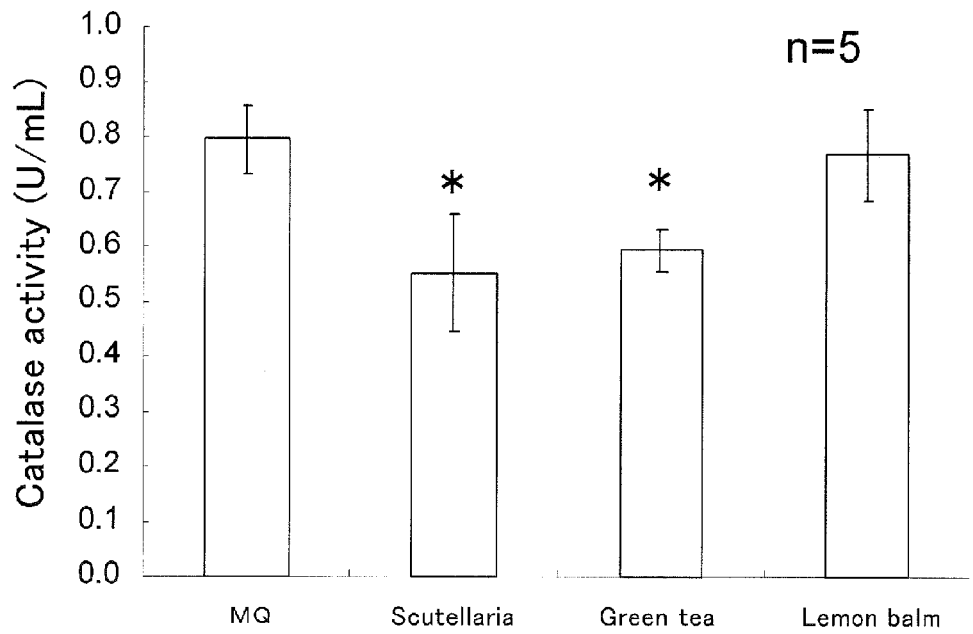
FIG. 3 is a graph showing catalase activity inhibitory actions of various crude drugs of which use as a catalase activity inhibitor of a sterilizer according to another embodiment of the present invention is examined.

ESR measurements of the obtained mixture liquid samples were conducted, and catalase activity was measured from FIG. 2 based on line widths of the ESR spectrums. The measurement results are shown in FIG. 3. As shown in FIG. 3, the significantly high catalase inhibitory actions of significance level of 5% were confirmed with scutellaria and green tea (* in FIG. 3). From the results, it can be said that *scutellaria* and green tea are suitable as the catalase activity inhibitors.

Example 3

An experiment for examining an effect of the catalase activity inhibitor of enhancing a sterilization effect was conducted. In the experiment, *Streptococcus aureus* which is a catalase-positive bacterium was used as a target of the sterilization. A bacterium suspension having a concentration of $10^7$ cells/mL was prepared by using the bacterium and saline, and the suspension was used for the experiment. A semiconductor laser (product name: RV-1000, Ricoh Optical Industries Co., Ltd.) was used as a light emitting device, in which an irradiation light wavelength was set to 400±20 nm, an irradiation output was set to 300 mW, and an irradiation time was set to two minutes. 100 μL of the bacterium suspension and 150 μL of hydrogen peroxide were mixed on a 96-well microplate to attain the final concentrations shown in Table 3. Experiment samples were prepared by using *scutellaria* as the catalase activity inhibitor, diluting the *scutellaria* with ultrapure water, followed by sterilization by filtration through a 0.22 μm filter, and then adding the *scutellaria* solution to the mixture liquids of bacterium suspension and hydrogen peroxide to attain final *scutellaria* concentrations of 0, 1, and 3 mg/mL.

TABLE 3

|  | Amount | Final concentration |
| --- | --- | --- |
| Bacterium Suspension | 100 μL | 1 CFU/mL |
| Scutellaria | 50 μL | 0, 1, and 3 mg/mL |
| Hydrogen peroxide | 150 μL | 1M |

The laser irradiation was performed immediately after preparing the experiment samples, and 50 μL of the sample after the irradiation and 50 μL of 5000 U/mL catalase were mixed to stop the reaction of hydrogen peroxide. After that, a 10-fold dilution series was prepared and was seeded on a BHI agar culture medium, followed by culturing under an aerophilic condition of 37° C. for 24 hours, and then evaluation of the sterilization effect was conducted. Also, the same experiment was conducted on the case of using *Candida albicans* which is a catalase-positive fungus as the sterilization target and green tea as the catalase activity inhibitor. Further, evaluations of sterilization effects varied by the lacking of hydrogen peroxide, catalase activity inhibitor, and/or laser irradiation were conducted as comparative experiments. Results of the experiments are shown in FIG. 4 to FIG. 6.

Figure 4:
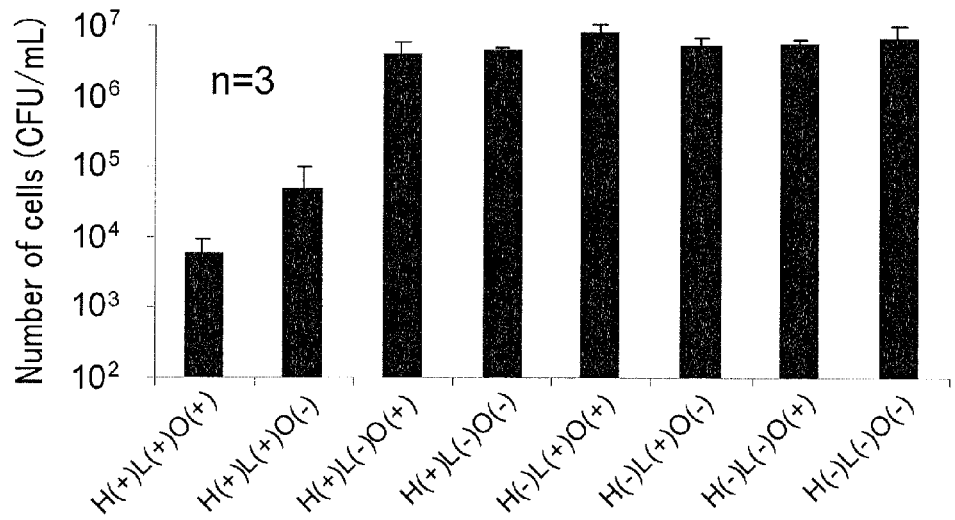
FIG. 4 is a graph showing an effect of enhancing a sterilization effect on Streptococcus aureus by scutellaria of the catalase activity inhibitor of the sterilizer according to the embodiment of the present invention (in the graph, H indicates hydrogen peroxide, L indicates laser irradiation, O indicates scutellaria (1 mg/mL), + indicates positive, and − indicates negative).

As shown in FIG. 4, it was confirmed that the sterilization effect on *Streptococcus aureus* attained in the case of adding *scutellaria* at the concentration of 1 mg/mL [H(+)L(+)O(+) in FIG. 4] is about 10 times of the case of not adding *scutellaria* [H(+)L(+)O(−) in FIG. 4]. Also, it was confirmed that no sterilization effect on *Streptococcus aureus* was attained in the case where *scutellaria* was used without using hydrogen peroxide [H(−)L(−)O(+) in FIG. 4], in the case where the light irradiation was performed only on *scutellaria* [H(−)L(+)O(+) in FIG. 4], in the case where only hydrogen peroxide is used [H(+)L(−)O(−) in FIG. 4], and in the case where the light irradiation was not performed [H(+)L(−)O(+) in FIG. 4].

Figure 5:
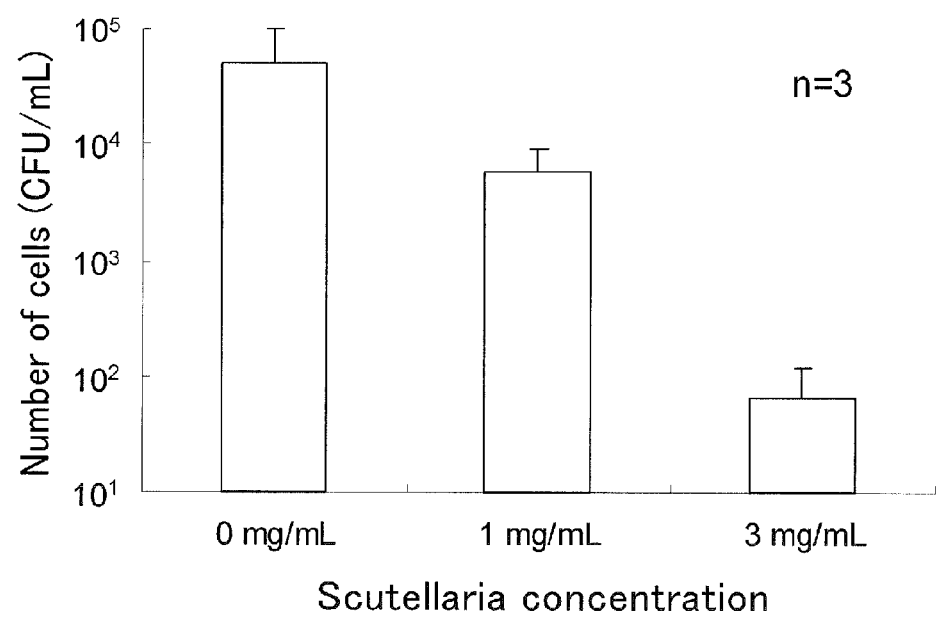
FIG. 5 is a graph showing sterilization effects which are exerted by the catalase activity inhibitor according to the embodiment of the present invention on Streptococcus aureus and vary depending on concentrations of scutellaria.

As shown in FIG. 5, it was confirmed that the sterilization effect on *Streptococcus aureus* is enhanced along with the increase in concentration of *scutellaria* in the case where the concentration of *scutellaria* in the catalase activity inhibitor was varied. For instance, the sterilization effect on *Streptococcus aureus* attained with the *scutellaria* concentration of 3 mg/mL was about 1000 times of the hydroxy radical sterilization (*scutellaria* concentration: 0 mg/mL) using hydrogen peroxide only and not using the catalase activity inhibitor.

Figure 6:
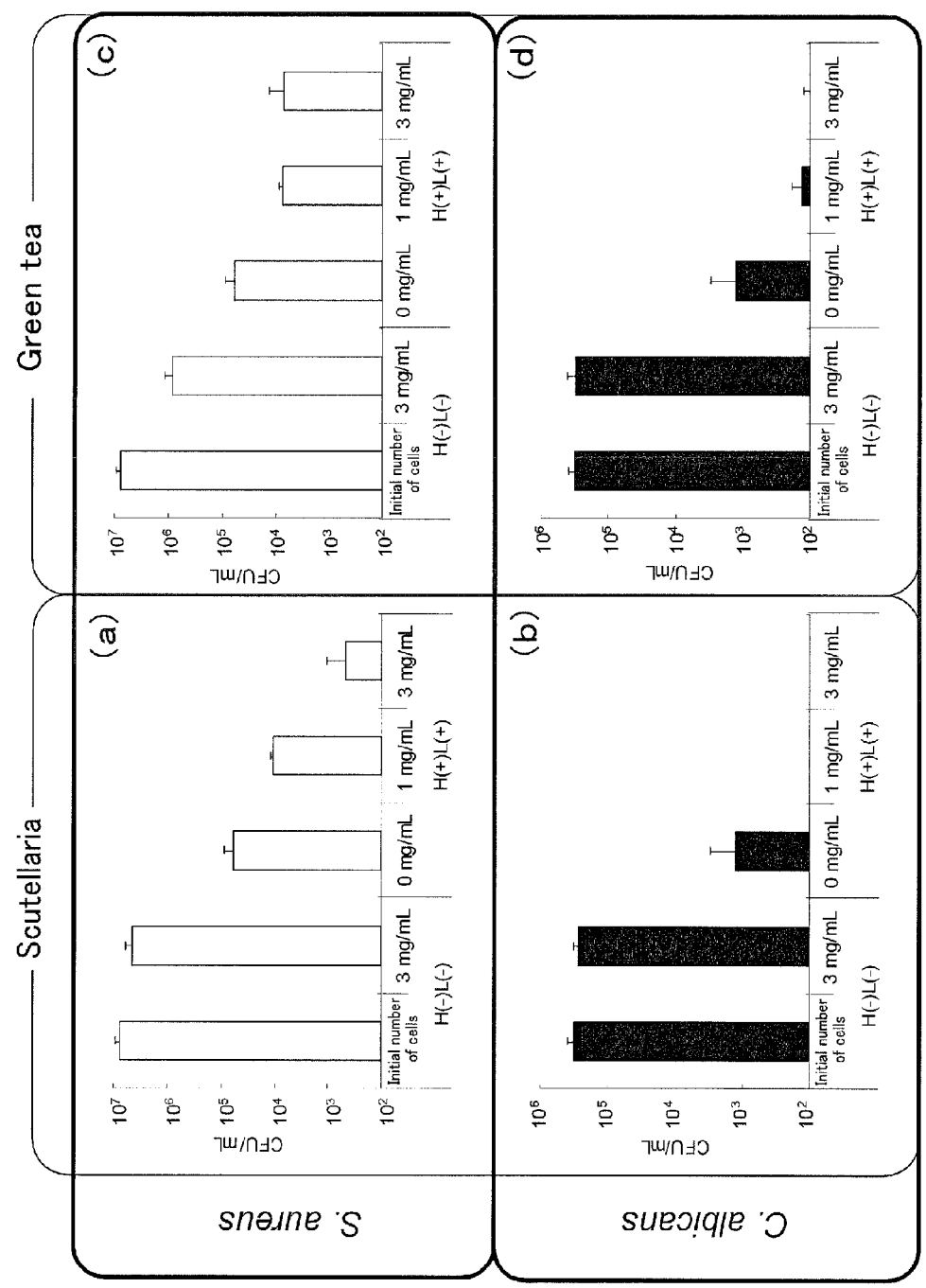
FIG. 6 is a graph showing sterilization effects which are exerted by the catalase activity inhibitor according to the embodiment of the present invention on (a) Streptococcus aureus and (b) Candida albicans, and vary depending on concentrations of scutellaria and sterilization effects which are exerted by the catalase activity inhibitor on (c) Streptococcus aureus and (d) Candida albicans and vary depending on concentrations of green tea (in the graph H indicates hydrogen peroxide, L indicates laser irradiation, + indicates positive, and − indicates negative).

Further, as shown in (a) and (b) of FIG. 6, it was confirmed that not only the sterilization effect on *Streptococcus aureus* but also the sterilization effect on *Candida albicans* are enhanced along with the increase in concentration of *scutellaria*. As shown in (c) and (d) of FIG. 6, it was confirmed that, in the case where the green tea was used as the catalase activity inhibitor, the sterilization effects on *Streptococcus aureus* and *Candida albicans* are enhanced along with the increase in concentration of green tea. Further, as shown in (a) to (d) of FIG. 6, the sterilization effect is dramatically enhanced by using the catalase activity inhibitor in combination with hydrogen peroxide and the laser irradiation.

From the results shown in FIG. 4 to FIG. 6, it can be said that more efficient sterilization is realized by using the catalase activity inhibitor in combination with the hydroxy radical sterilization employing the photolysis of hydrogen peroxide. Also, since it is said that there is a correlation between catalase activity of a bacterium and pathogenicity and that a bacterium having a strong defense mechanism against oxidative stress is highly likely to cause an infection, it can be said that the present invention employing the combined use of the catalase activity inhibitor is effective for sterilization of the bacterium having high pathogenicity.

The invention claimed is:

1. A sterilization method comprising:
    contacting a sterilizer comprising hydrogen peroxide and a catalase activity inhibitor, as initial reagents, with a sterilization target, and
    irradiating the sterilization target with light having a wavelength in a range of from 350 nm to 500 nm,
    wherein the catalase activity inhibitor comprises *scutellaria* or green tea.

2. The sterilization method according to claim 1, wherein the catalase activity inhibitor is *scutellaria*.

3. The sterilization method according to claim 1, wherein the sterilization target is irradiated for two minutes.

4. A sterilizer evaluation method comprising:
    performing an electron spin resonance (ESR) measurement of a liquid mixture of a sample collected from a sterilization target brought into contact with a sterilizer and 4-hydroxy-2,2,6,6-tetramethylpiperidine N-oxide (TEMPOL), and
    evaluating a sterilization effect of the sterilizer by performing a measurement of catalase activity of cells or microorganisms contained in the sample based on a line width of an obtained electron spin resonance (ESR) spectrum,
    wherein the sterilizer comprises: (i) hydrogen peroxide, and (ii) a catalase activity inhibitor comprising *scutellaria* or green tea, as initial reagents, which is configured to be brought into contact with a sterilization target and then irradiated with light having a wavelength in a range of from 350 nm to 500 nm.

5. The sterilizer evaluation method according to claim 4, wherein the sterilizer is an oral cavity sterilizer.

6. The sterilizer evaluation method according to claim 4, wherein the catalase activity inhibitor is *scutellaria*.

\* \* \* \* \*